United States Patent [19]

Reid

[11] Patent Number: 5,067,482
[45] Date of Patent: Nov. 26, 1991

[54] CONCEALED FACIAL SKIN UPLIFTING DEVICE

[76] Inventor: Helen B. Reid, The Summit, #2701, 999 Green St., San Francisco, Calif. 94133

[21] Appl. No.: 657,171
[22] Filed: Feb. 15, 1991
[51] Int. Cl.⁵ .............................................. A61F 5/08
[52] U.S. Cl. ................................. 128/76 B; 128/76 R
[58] Field of Search ..................... 128/76 R, 76 B, 163

[56] References Cited

U.S. PATENT DOCUMENTS

| | | | |
|---|---|---|---|
| 1,559,732 | 11/1925 | Arnold | 128/76 |
| 1,643,090 | 9/1927 | Rogers | 128/76 B |
| 1,654,560 | 1/1928 | Sterling | 132/48 |
| 1,765,451 | 6/1930 | Holmes . | |
| 2,595,462 | 5/1952 | Johnson | 24/115.8 |
| 2,871,540 | 2/1959 | Smith | 24/237 |
| 2,896,613 | 7/1959 | Brown | 128/76 |
| 3,154,071 | 10/1964 | Haagen | 128/76 |
| 3,524,443 | 8/1970 | Batlin | 128/76 |
| 3,565,164 | 4/1971 | Heale | 128/76 |
| 3,584,619 | 6/1971 | Bowser, Jr. | 128/76 B |
| 3,672,363 | 6/1972 | Masters | 128/76 |
| 3,736,925 | 6/1973 | Erman | 128/76 |
| 3,782,372 | 1/1974 | Carlton | 128/76 |
| 4,239,037 | 12/1980 | Fausone | 128/76 |

FOREIGN PATENT DOCUMENTS 217083 6/1924 United Kingdom .............. 128/76 B
736967 9/1955 United Kingdom .............. 128/76 B

OTHER PUBLICATIONS

Applicants's prior model of facial skin uplifting device.

Primary Examiner—Richard J. Apley
Assistant Examiner—Linda C. M. Dvorak
Attorney, Agent, or Firm—Flehr, Hohbach, Test, Albritton & Herbert

[57] ABSTRACT

A device for uplifting facial skin which includes adhesive pads and a nylon line secured over the wearer's head. Upward pulling forces are applied by the line through an elastomeric tension strap which is light or flesh toned color for purposes of concealment. The lower end of the tension strap is releasably mounted to the upward end of a T-bar connector which is formed of a transparent, compliant material. The upper margin of each pad is wrapped over and secured to a crossbar on the lower end of the connector so that the pulling forces are evenly distributed across the width of the pad. When adhering to the facial skin the pads are adjusted to the desired position by a releasable clip through which the nylon line is secured.

6 Claims, 1 Drawing Sheet

CONCEALED FACIAL SKIN UPLIFTING DEVICE

BACKGROUND OF THE INVENTION

This invention relates in general to facial uplifting devices of the type used by people who desire to improve their appearance by eliminating the effects of facial skin which is wrinkled or sagging.

Heretofore facial uplifting devices have been provided for use by individuals to remove lines, wrinkles and sagging in the facial skin. Among the prior art devices is the Batlin U.S. Pat. No. 3,524,443 which issued to the present inventor. In the Batlin patent facial skin is uplifted by adhesive pads secured to connector strips which in turn are attached to a nylon line mounted about the wearer's head. A spring wire retaining clip adjusts tension on the line and is concealed within the wearer's hair. Other skin uplifting devices include the Haagen U.S. Pat. No. 3,154,071 which provides adhesive tabs secured to elastic bands which run through the hair, and the Carlton U.S. Pat. No. 3,782,372 which provides adhesive pads pulled upwardly by cords. The Fausone U.S. Pat. No. 4,239,037 provides pads which are attached through hook and loop fastening strips to a comb within the hairpiece. The Erman U.S. Pat. No. 3,736,952 provides a plurality of adhesive pads attached through elastic lines to a plate within the hair. The Brown U.S. Pat. No. 2,896,613 provides adhesives pads which are attached through elastic tension members which in turn are connected to a comb within the hair.

Prior art facial uplifting devices of the type described have a number of disadvantages and drawbacks. When in use, the prior art devices are difficult to conceal from view, which is cosmetically objectionable. Another problem in the prior art devices is that the skin underlying and adjacent the adhesive pads tends to wrinkle when the wearer's face moves, such as when speaking, laughing or smiling. Yet another problem is that the distribution of uplifting force is not uniform across the adhesive pads, with the result that the underlying skin is not uniformly pulled upwardly. The prior devices can also be uncomfortable, especially when the wearer's face moves as when speaking, laughing or smiling.

OBJECTS AND SUMMARY OF THE INVENTION

It is therefore a general object of the present invention to provide a new and improved device for uplifting facial skin for improving the wearer's appearance and comfort.

Another object is to provide a facial uplifting device of the type described which is substantially concealed and almost invisible from view when in use.

Another object is to provide a facial uplifting device of the type described which permits freedom of movement of the facial skin such as when the person is speaking, laughing or smiling.

Another object is to provide a facial uplifting device of the type described with improved means for attaching the adhesive pads to the supporting nylon line.

The invention in summary provides a concealed facial uplifting skin device which includes a pair of adhesive coated transparent pads adapted for releasable attachment to the wearer's facial skin. The pads are connected by means of transparent, compliant T-shaped connectors to elongate, flat tension strips which in turn are connected to the opposite ends of a nylon line. The tension strips are connected to shanks of the connectors. Upper margins of the pads are wrapped around crossbars of the connectors. With the line secured about the wearer's head, upward pulling forces are applied through the tension strips and connectors so that the crossbars transmit the pulling forces uniformly across the width of the pads to the underlying skin. When in place the components of the device are concealed and made almost invisible from view.

The foregoing and additional objects and features of the invention will appear from the following specification in which the several embodiments have been set forth in detail in conjunction with the accompanying drawings.

DETAILED DESCRIPTION

Figure 1:
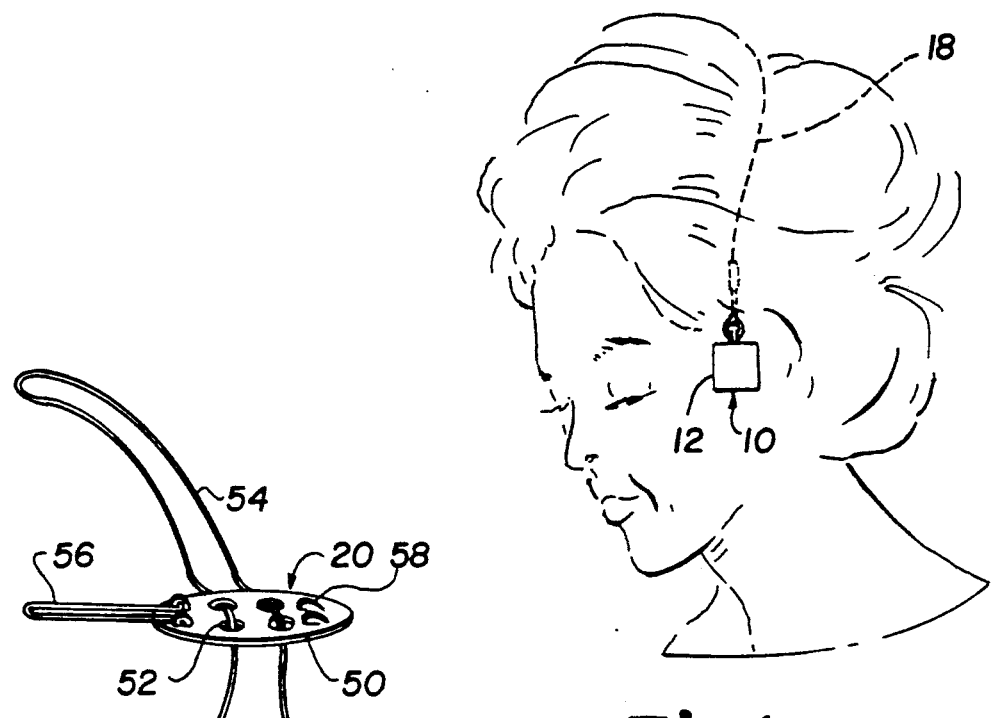
FIG. 1 is a perspective view illustrating attachment of the uplifting device of the invention about a wearer's head.
Figure 2:
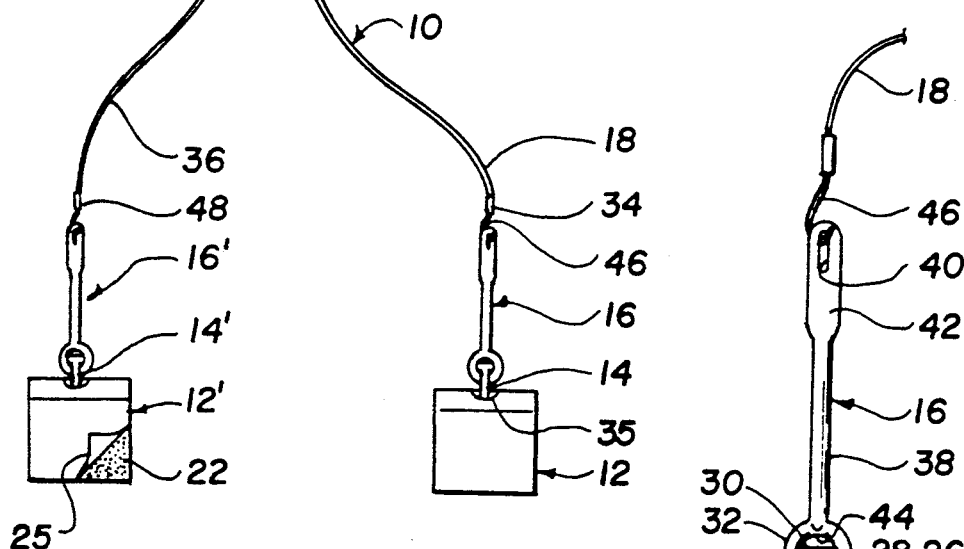
FIG. 2 is a perspective view illustrating the facial uplifting device of the invention.

In the drawings FIGS. 1 and 2 illustrate generally at 10 the facial uplifting device according to a preferred embodiment of the invention. Device 10 is comprised of a pair of flat adhesive pads 12, 12', T-shaped connectors 14, 14', tension strips 16, 16', nylon line 18 and adjustment clip assembly 20.

Each adhesive pad 12, 12', is of generally rectangular shape, and one side has a pressure-sensitive adhesive coating 22 suitable for adhering with facial skin. The material of the pads and adhesive coating are transparent for purposes of concealment. A plurality of pinhole sized apertures 24 are formed in a pattern through the pads for permitting air to reach the skin and prevent irritation. Prior to use the adhesive coatings are covered by a layer of peel-off protective paper backing 25, as shown in FIG. 2.

Figure 3:
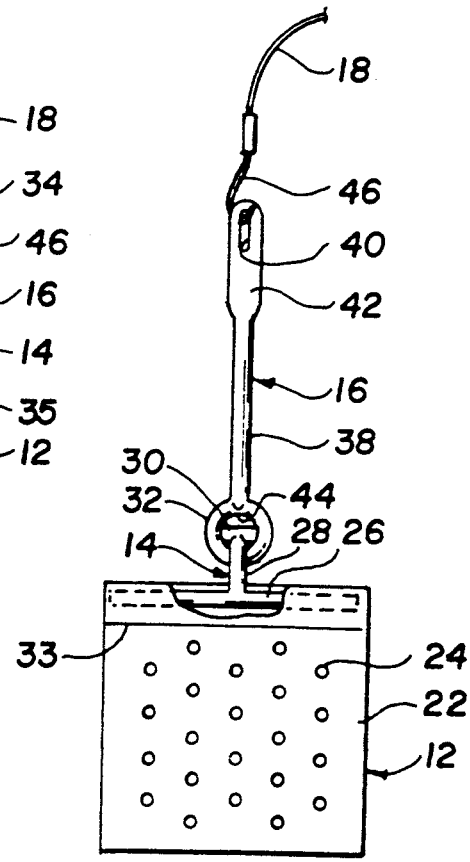
FIG. 3 is a plan view, to an enlarged scale, of component elements of the device of FIG. 1.

Each pad is secured at its upper end to one of the flat, T-shaped connectors 14, 14'. As shown in FIG. 3, the connector 14 is comprised of a lateral crossbar 26 and a shank 28 which extends orthogonally from the mid-portion of the crossbar. A holding bar 30 is formed integral at the upward end of the shank for releasable attachment through an eyelet 32 at the lower end of a respective tension strip. The connectors are formed of a transparent, compliant material which has sufficient strength to apply the upward pulling forces to the pads. A compliant transparent plastics material is suitable for this purpose. The compliant property of the plastic permits the connector to yieldably change shape when stressed, such as from movement of the wearer's skin. This permits the facial skin to move while the pads stay in place, thereby allowing for facial movement while the wearer is speaking, laughing or smiling. The flat shape and transparent nature of the material assists in concealing the connectors, thus rendering it nearly invisible.

The pad is secured to the crossbar by means of the pad upper margin 33 the adhesive side of which is folded around the crossbar and secured back against the standing portion of the pad. This captures the crossbar within the folded margin. Shank 28 of the connector penetrates through a small opening 35 which is formed in the folded margin.

Tension strips 16, 16', provide the links between the T-shaped connectors and the opposite ends 34, 36 of nylon line 18. Each connector has an elongated shank 38 formed at its upper end with an attachment opening 40 which penetrates through a vertically elongate, oval-shaped reinforcing head 42. The tension strips are formed of an elastomeric material, such as rubber, having sufficient strength to transmit the pulling forces while permitting a limited range of movement of the adhesive pads. The surfaces of the tension strips have a suitable light color, such as flesh tone, so that they are not visible when in use. The opening 44 in eyelet 32 is sized smaller than the width of holding bar 30 so that it can be fitted over and captured on the bar to exert the pulling force.

The tension strips 16, 16' are releasably secured to the lower ends of the nylon line by a pair of flat hooks 46, 48. The hooks are formed of a suitable plastics material which is transparent. The ends of the hooks releasably mount through attachment openings 40 at the upper end of the tension strips.

The nylon line is gathered and adjustably secured above the wearer's head by means of the clip assembly 20. The clip assembly is comprised of a small oval plate 50 having two pairs of spaced holes 52 through which a mid-portion 54 of the line is threaded. A spring metal retainer 56 is hingeably mounted to one side of the plate, and when the retainer pivots down its distal end releasably engages with a boss 58 formed at the opposite end of the plate. When the retainer is engaged with the boss it presses against and holds the line from movement through the plate holes.

In use of device 10, the facial skin is first prepared by means of suitable cleansing pads, not shown. Nylon line 18 is then draped over the wearer's head with the adhesive pads 12 and 12' hanging down along the sides of the face. With the retainer 56 of clip 20 open, the nylon line is pulled through the plate holes to move the pads to the approximate desired position along the face.

The protective paper backing 25 on the adhesive pads is then peeled off, and the pads are applied to the skin by a gentle, rubbing pressure of the fingers. With the wearer's hair held away from clip and the mid-portion of the nylon line held upwardly, the clip is slid down toward the scalp. With the clip held in place by one hand, the other hand is used to pull one side of the line upwardly through plate 50 to draw that side's adhesive pad and underlying skin upwardly to the desired position. The other side of the line is then similarly drawn upwardly to position the opposite adhesive pad. Retainer 56 is then closed to lock the lines in place, and the loose end of the line is wrapped and fastened around the clip, such as with a bobby pin. The hair is then brushed or combed to conceal the clip, the nylon line, and other components of the device as required to attain near invisibility.

While the foregoing embodiment is at present considered to be preferred it is understood that numerous variations and modifications may be made therein by those skilled in the art and it is intended to cover in the appended claims all such variations and modifications as fall within the true spirit and scope of this invention.

What is claimed is:

1. A device for uplifting the facial skin of a wearer, the device comprising the combination of a pair of transparent pads having flat sides and a coating of adhesive on one side of each pad for releasably securing the pad to the underlying facial skin, a pair of flat, T-shaped connectors, each connector comprised of a crossbar integrally formed with a shank which extends orthogonally from the mid-portion of the crossbar, said connectors being formed of a compliant material which permits the crossbar and shank to yieldably change shape when stressed due to movement of the wearer's skin, said material of the connectors further being substantially transparent for concealing the connectors from view, means for securing the crossbar of each connector to an edge of each pad along substantially the entire lateral width of the pad whereby upward pulling forces applied to the connector are transferred uniformly to the pad across its width and thence to the facial skin over the entire area of the skin underlying the pad, an elongated flexible line of a length sufficient to extend over the wearer's head, said line having a pair of ends which hang down adjacent to the wearer's hairline on opposite sides of the face, a pair of elongated, flat tension strips having upper and lower ends, each strip being formed of a flexible elastomeric material which is light colored for reducing its visibility when in use, means for releasably attaching the upper end of the shank of each connector to the lower end of a respective one of the tension strips, means for releasably attaching the upper end of each tension strip to a respective one of the ends of said line, and clip means for gathering and adjustably securing a mid-portion of said line above the wearer's head concealed within the hair whereby the ends of the line apply upward pulling forces through the tension strips, connectors and adhesive pads to uplift the portions of the facial skin which underlie the pads.

2. A facial skin uplifting device as in claim 1 in which the upper end of each tension strip is formed with an attachment opening and a vertically elongated, oval-shaped portion surrounding and reinforcing said attachment opening, said means for releasably attaching said ends of the lines through respective attachment openings of the tension strips.

3. A facial uplifting device as in claim 2 in which said means for releasably attaching the ends of the line includes a flat, substantially transparent hook releasably mounted in said attachment opening with the corresponding end of the line secured to the hook.

4. A facial uplifting device as in claim 1 in which the means for securing the crossbar of each connector to the upper edge of each pad includes a margin of the pad across the width of its upper edge with the adhesive side of the margin folded around the crossbar and secured to another portion of the pad whereby the crossbar is captured within the folded margin.

5. The facial uplifting device as in claim 1 in which a plurality of perforations are formed through the pads for permitting air to reach the underlying skin and thereby obviate skin irritation.

6. A facial uplifting device as in claim 1 in which the peripheral edges each pad define a rectangle.

* * * * *